(12) United States Patent
Heacock

(10) Patent No.: US 11,467,422 B2
(45) Date of Patent: Oct. 11, 2022

(54) CARBON DIOXIDE SENSING COLOR CHANGEABLE DYES FOR INDICATING EXPOSURE, METHODS OF MAKING AND USING SUCH DYES, AND APPARATUSES INCORPORATING SUCH DYE

(71) Applicant: Sensor International, LLC, Snoqualmie, WA (US)

(72) Inventor: Gregory Heacock, Maple Valley, WA (US)

(73) Assignee: SENSOR INTERNATIONAL, LLC, Snoqualmie, WA (US)

(*) Notice: Subject to any disclaimer, the term of this patent is extended or adjusted under 35 U.S.C. 154(b) by 94 days.

(21) Appl. No.: 14/292,246

(22) Filed: May 30, 2014

(65) Prior Publication Data

US 2015/0346513 A1 Dec. 3, 2015

(51) Int. Cl.
| | |
|---|---|
| *G02C 7/04* | (2006.01) |
| *G01N 33/52* | (2006.01) |
| *A61B 17/3211* | (2006.01) |
| *A61B 90/00* | (2016.01) |

(52) U.S. Cl.
CPC ............ *G02C 7/04* (2013.01); *A61B 17/3211* (2013.01); *G01N 33/52* (2013.01); *G02C 7/049* (2013.01); *A61B 2090/0807* (2016.02); *A61B 2090/0814* (2016.02); *Y10T 436/204998* (2015.01)

(58) Field of Classification Search
CPC .... G01N 31/22; G01N 31/223; G01N 31/224; G01N 33/004; G01N 33/52; G02C 7/04
USPC .............. 359/159.01, 159.02, 159.24, 159.3, 359/159.32; 600/300, 353; 435/4
See application file for complete search history.

(56) References Cited

U.S. PATENT DOCUMENTS

| | | | |
|---|---|---|---|
| 3,018,611 A | 1/1962 | Biritz | |
| 2,768,976 A | 10/1973 | Hu | |
| 3,768,976 A | 10/1973 | Hu | |
| 3,899,295 A | 8/1975 | Halpern | |

(Continued)

FOREIGN PATENT DOCUMENTS

| | | |
|---|---|---|
| CN | 101479584 | 7/2009 |
| CN | 101501468 | 8/2009 |

(Continued)

OTHER PUBLICATIONS

Extended Supplementary European Search Report, EP Application No. EP07864168, dated Mar. 1, 2011.

(Continued)

*Primary Examiner* — Ephrem Z Mebrahtu
(74) *Attorney, Agent, or Firm* — McAndrews, Held & Malloy, Ltd.

(57) ABSTRACT

According to embodiments of the present application, a carbon dioxide sensing color changeable dye can comprise a carbon dioxide status indicator, a solvent, a polymer wherein the carbon dioxide status indicator is dispersed, an optional plasticizer, and an optional agent to facilitate mixing. The color changeable dye is a first color in the presence of a carbon dioxide rich environment and is capable of changing to a second color upon exposure to atmospheric condition for a period of time corresponding to the intended use time of a restricted, disposable or limited use product. Methods of making and using the color changeable dye and apparatuses incorporating such dye are also disclosed.

6 Claims, 22 Drawing Sheets

(56) References Cited

U.S. PATENT DOCUMENTS

| | | |
|---|---|---|
| 3,939,968 A | 2/1976 | Ryder |
| 4,003,709 A | 1/1977 | Eaton |
| 4,098,577 A * | 7/1978 | Halpern ............... A61L 2/28 436/1 |
| 4,135,792 A | 1/1979 | Deeg et al. |
| 4,526,752 A | 7/1985 | Perlman et al. |
| 4,692,309 A | 9/1987 | Pannwitz |
| 4,728,499 A | 3/1988 | Fehder |
| 5,159,360 A | 10/1992 | Stoy et al. |
| 5,518,927 A | 5/1996 | Malchesky et al. |
| 5,623,323 A | 4/1997 | Johnson et al. |
| 5,706,073 A | 1/1998 | Volk |
| 5,942,438 A | 8/1999 | Antonoplos et al. |
| 6,060,210 A | 5/2000 | Eda et al. |
| 6,114,509 A | 9/2000 | Olsen et al. |
| 6,132,086 A | 10/2000 | Henwood |
| 6,218,189 B1 | 4/2001 | Antonoplos et al. |
| 6,254,969 B1 | 7/2001 | Eberle |
| 6,270,724 B1 * | 8/2001 | Woodaman ............ G01N 33/02 116/106 |
| 6,518,231 B2 | 2/2003 | Appel et al. |
| 6,634,747 B1 | 10/2003 | Atkins et al. |
| 6,634,753 B1 | 10/2003 | Rozenman |
| 6,710,221 B1 | 3/2004 | Pierce et al. |
| 6,790,411 B1 | 9/2004 | Read |
| 6,851,808 B2 | 2/2005 | Heacock |
| 7,219,799 B2 | 5/2007 | Bonnette et al. |
| 7,244,252 B2 | 7/2007 | Berndt |
| 7,785,299 B2 | 8/2010 | Crawford et al. |
| 8,137,303 B2 | 3/2012 | Crawford et al. |
| 8,163,237 B2 | 4/2012 | Crawford et al. |
| 8,257,663 B2 | 9/2012 | Crawford et al. |
| 8,338,131 B2 | 12/2012 | Callen et al. |
| 8,388,131 B2 | 3/2013 | Heacock |
| 8,663,998 B2 | 3/2014 | Heacock |
| 2002/0022008 A1 | 2/2002 | Forest |
| 2002/0023642 A1 | 2/2002 | Allard et al. |
| 2002/0137123 A1 | 9/2002 | Hui |
| 2003/0199095 A1 * | 10/2003 | Yuyama ............... G01N 31/223 436/1 |
| 2004/0115319 A1 | 6/2004 | Morris |
| 2004/0180391 A1 | 9/2004 | Gratzl et al. |
| 2005/0041200 A1 | 2/2005 | Rich |
| 2005/0125924 A1 | 6/2005 | Benjamin et al. |
| 2005/0164898 A1 | 7/2005 | Katsuri et al. |
| 2006/0046301 A1 | 3/2006 | Happe |
| 2006/0054525 A1 | 3/2006 | Dean et al. |
| 2006/0054526 A1 | 3/2006 | Dean |
| 2006/0069305 A1 | 3/2006 | Couvillon et al. |
| 2006/0110835 A1 | 5/2006 | Gohil |
| 2006/0181676 A1 | 8/2006 | Tucker et al. |
| 2006/0236913 A1 | 10/2006 | Wills |
| 2007/0017042 A1 | 1/2007 | Cincotta et al. |
| 2007/0140911 A1 | 6/2007 | Carney et al. |
| 2008/0081020 A1 | 4/2008 | Huang |
| 2008/0129960 A1 * | 6/2008 | Heacock ............ A61B 17/3211 351/159.31 |
| 2009/0266289 A1 | 10/2009 | Greene |
| 2009/0301382 A1 | 12/2009 | Patel |
| 2009/0303440 A1 | 12/2009 | Heacock et al. |
| 2010/0112680 A1 | 5/2010 | Brockwell et al. |
| 2010/0224508 A1 * | 9/2010 | Yuyama ............... G01N 31/223 206/0.6 |
| 2011/0130727 A1 | 6/2011 | Crawford et al. |
| 2011/0130728 A1 | 6/2011 | McKinnon et al. |
| 2011/0259086 A1 | 10/2011 | Harris et al. |
| 2012/0276647 A1 | 1/2012 | Mills |
| 2013/0130399 A1 | 5/2013 | Mills |
| 2013/0150785 A1 | 6/2013 | Heacock |
| 2013/0269592 A1 | 10/2013 | Peacock et al. |
| 2013/0293353 A1 | 11/2013 | McPherson |
| 2014/0296402 A1 * | 10/2014 | Jung ................... C09D 133/14 524/159 |
| 2015/0087076 A1 | 3/2015 | Heacock |
| 2015/0225304 A1 * | 8/2015 | Donze ................... C05D 9/00 71/23 |
| 2015/0253252 A1 | 9/2015 | Smyth |
| 2016/0011157 A1 * | 1/2016 | Smyth ................. G01N 31/229 422/426 |
| 2016/0327491 A1 * | 11/2016 | Wood ................. B01D 46/0086 |

FOREIGN PATENT DOCUMENTS

| | | |
|---|---|---|
| EP | 0231499 | 8/1987 |
| EP | 2021755 | 5/2007 |
| WO | WO 02/099416 A1 | 12/2002 |
| WO | 2004077035 | 9/2004 |
| WO | 2007/018301 | 2/2007 |
| WO | 2008095960 | 8/2008 |
| WO | 2013/085655 | 6/2013 |
| WO | 2013085655 A1 | 6/2013 |
| WO | WO-2014020326 A2 * | 2/2014 ............ A61B 42/00 |
| WO | 2015048138 A1 | 4/2015 |

OTHER PUBLICATIONS

International Search Report and Written Opinion in International Application No. PCT/US2012/63797, dated Jan. 17, 2013. (10 pages).

International Search Report and Written Opinion in International Application No. PCT/US2007/84186, dated Sep. 2, 2008.

Michael Freemantle, Intelligence Ink Detects Oxygen, Chemical Gas Sensing, Aug. 2, 2004, p. 11, vol. 82, No. 31, Chemical & Engineering News USA.

International Preliminary Report on Patentability in PCT/US2007/084186, dated Jun. 11, 2009, 12 pages.

International Preliminary Report on Patentability in PCT/US2012/063797, dated Jun. 19, 2014 (10 pages).

Swann et al., "Designing Out Curative Syringe Reuse: Maximising Global Acceptance and Impact by Design," Internet Citation, http://eprints.hud.ac.uk/11783/ [dated Sep. 19, 2013] abstract.

The Guardian, Architecture and Design Blog with Oliver Wainwright, "How colour-changing technology could revolutionise the medical industry," Internet Citation, http://www.theguardian.cco/artanddesign/architectarc-design-blog/2013/aug/28/colour-changing-syringe-medical-design [dated Sep. 18, 2013].

European Patent Office, Communication with extended European search report, in Application No. 14166858.2, dated Sep. 4, 2014 (7 pages).

PCT, Notification of Transmittal of the International Search Report and the Written Opinion of teh International Searching Authority, in Application No. PCT/US2015/032885, dated Aug. 14, 2015 (10 pages).

European Patent Office, Communication with extended European search report in application No. 12855085.2, dated Aug. 3, 2015 (6 pages).

PCT, Notification of Transmittal of the International Search Report and the Writen Opinion of the International Searching Authority, or the Declaration, in Application No. PCT/US14/57225, dated Dec. 17, 2014 (11 pages).

European Patent Office Office Action, dated May 24, 2017, re: Applicant: Sensor International, LLC, Application No. 14847026.3-1554/3049135 PCT/US2014057225 (13 pages).

Non Final Office Action dated Jan. 6, 2016.

Final Office Action dated Sep. 6, 2016.

Non Final-Office Action dated Jan. 13, 2017.

PCT, International Search Report, Application No. PCT/US2014/057225, dated Dec. 17, 2014, 2 pages.

PCT, Written Opinion of the International Searching Authority, Application No. PCT/US2014/057225, dated Dec. 17, 2014, 4 pages.

PCT, International Search Report, Application No. PCT/US2015/032885, dated May 28, 2015, 2 pages.

PCT, Written Opinion of the International Searching Authority, Application No. PCT/US2015/032885, dated May 28, 2015, 5 pages.

(56) References Cited

OTHER PUBLICATIONS

European Patent Office, Communication with extended European Search Report, in Application No. 15800286.5 dated Dec. 7, 2017.
Extended European Search Report for Patent No. 14847026.3 dated Aug. 25, 2017.
Japanese Patent Office Official Action, dated Oct. 30, 2018, Japanese Patent Application No. 2017-515011.
EPO Communication from European Patent Office, dated Jan. 29, 2020, European Application No. 15800286.5-113.

* cited by examiner

CARBON DIOXIDE SENSING COLOR CHANGEABLE DYES FOR INDICATING EXPOSURE, METHODS OF MAKING AND USING SUCH DYES, AND APPARATUSES INCORPORATING SUCH DYE

BACKGROUND OF THE APPLICATION

Generally speaking, the present application relates to a carbon dioxide sensing color changeable dye that changes color after being exposed to an atmosphere for a predetermined period of time. In one embodiment, the color changeable indicator is intended for use on or in disposable, limited or restricted use products that can transmit contaminants or disease to a person, cause infection, or decline in quality or potency if reused or used beyond a recommended period of time. In another embodiment, the color changeable indicator is intended for use on or in packaging for a product for human consumption wherein the product for human consumption can decline in freshness, quality of taste, and/or potency and/or can cause disease if consumed beyond a recommended period of time. The color changeable indicator also acts to indicate that a product should no longer be used or consumed. The present application also relates to methods of making and using the color changeable dye and apparatuses incorporating the color changeable dye.

Many products currently marketed and sold are designed for limited use. These products are usually associated with a single event, a restricted time period or restricted access. There are many reasons for the need of single use or limited use products.

There are numerous examples of single use products in the medical field. One example is a disposable syringe. Instrument contamination and cross infection between patients is an ever present concern if the syringe is inadvertently reused. It is a particular concern in some countries where repeated use of instruments is known to transmit serious diseases such as HIV and hepatitis. Medical and ophthalmic devices that must be sterilized such as scalpels or tonometers (e.g., for the measurement of a patient's intraocular pressure) body piercing and tattooing instruments used on multiple clients also give cause for concern. Needles used in acupuncture offer another example. Decontamination procedures or employment of single-use devices are methods used to control cross infection, but they rely on personnel awareness, willingness to follow protocol, monitoring and documentation.

The limited use type of product is usually associated with goods that should be used for a restricted time period. One example of this type of product is "daily wear" or disposable contact lenses. Contact lenses for refractive correction or cosmetic purposes require suitable wear and care regimes in order to maintain good eye health. Non-compliance on the part of the patient, either through choice or due to lack of education, can injure the eye. Frequent replacement lenses are sometimes worn for longer than recommended or they may be stored or cleaned inappropriately.

Other examples of limited use products that have a shelf life after which they should not be used because of a risk of infection or a decrease in effectiveness are cosmetic products, personal hygiene products such as electric toothbrush heads, and home diagnostic kits such as pregnancy tests and ovulation prediction tests. For example, it has been found that cosmetic applicators can harbor bacteria that can infect the eye and should be disposed of prior to their expiration to prevent eye infections.

Many products currently marketed and sold to consumers are supplied prepackaged where the packaging is intended to preserve the freshness of the product such as food or beverages or in the case of medication, the potency of the content within the packaging. These products are usually associated with a single event, i.e., the contents remain fresh or potent until the packaging is opened by the consumer; however, the freshness or quality of the contents may decrease over time.

An example of the importance of preservation of a packaged product is a cold tablet or a food item. Medicinal potency or food spoilage and the expense related to these issues are important to both consumers and manufacturers. Pharmaceuticals, food stuff, and similar items are commonly packaged in sealed plastic containers.

Gas, such as oxygen, permeation through the plastic material of the container negatively affects the freshness or quality of the contents of many packaged products. In the case of pharmaceuticals, oxygen absorption decreases potency. In the case of food products, oxygen absorption into the packaged food makes the food taste stale. Other products and items also have limited use where quality of the item decreases over time.

U.S. Pat. No. 8,388,131 and its related cases, which are co-owned by applicant and incorporated herein in its entirety by reference, previously addressed a similar problem. U.S. Pat. No. 8,388,131 and its related cases presented, for example, a disposable limited or restricted use apparatus that includes a color changeable portion wherein the time that the color change occurs is controlled so that it coincides to the approximate time of the end of one use of a single use apparatus or to the approximate expiration time for extended but limited or restricted use apparatus.

U.S. Pat. No. 8,663,998, which is co-owned by applicant and incorporated herein in its entirety by reference, also addressed a similar problem. U.S. Pat. No. 8,663,998 is directed to, for example, a color changeable dye that can include a redox indicator, a reduction reaction initiator, an electron donor, an oxygen scavenger, an indicator barrier agent, a thickening agent and an agent to facilitate mixing. The color changeable dye may be, for example, a first color in the presence of oxygen, capable of changing to a second color upon reduction in a substantially oxygen free environment, and capable of changing back to the first color after exposure to oxygen for a period of time corresponding to the intended use time of a disposable or limited use product.

U.S. patent application Ser. No. 14/038,586, which is co-owned by applicant and incorporated herein in its entirety, is directed to, for example, use protocol indicators having a color changeable dye that changes color after exposure to a particular environment for a defined time. U.S. patent application Ser. No. 14/038,586 is also directed to, for example, an exposure time indicator that uses a color changeable dye or multiple color changeable dyes that change color after exposure to an environment in a sequential manner.

The present application addresses the benefit of allowing the color changeable dye to be applied to a disposable, limited or restricted use apparatus in a carbon dioxide environment. When the color changeable dye is later exposed to an environment having a different level of carbon dioxide for a period of time it changes color indicating that the disposable or limited use product should no longer be used.

BRIEF SUMMARY OF THE APPLICATION

The present application relates to a color changeable dye that comprises a carbon dioxide status indicator, a solvent, and a polymer wherein the carbon dioxide status indicator is dispersed.

The color changeable dye can be a first color in the presence of a higher than atmospheric carbon dioxide environment, and can be capable of changing to a second color after exposure to atmospheric conditions for a period of time corresponding to the intended use time of a restricted, disposable or limited use product. In one example, the period of time is less than about 60 minutes. In another example, the period of time is between about 1 and about 168 hours.

Examples of carbon dioxide status indicators include Cresol Red, Texas Red Hydrazine, Bromothymol Blue, M-Cresol Purple, Phenol Red, Congo Red and Natural Red.

Examples of solvents include acetone, alcohol, ethanol, methanol and water.

Examples of polymers include polyvinyl alcohol (PVA), hydroxyethyl cellulose (HEC), hydroxypropyl cellulose (HPC), polyvinyl butyral (PVB), polyvinyl chloride (PVC), polyethylene terephthalate (PET), and polymers made from vinylidene chloride along with other monomers.

The color changeable dye can further comprise a plasticizer and/or an agent to facilitate mixing. In one example, the plasticizer is glycerol. Examples of agents to facilitate mixing are bentonite nanoclay, glass microspheres, diatomaceous earth and cellulose acetate.

According to embodiments of the present application, a disposable ophthalmic or medical apparatus comprises a disposable ophthalmic or medical device and a color changeable dye disposed on the device wherein the color changeable dye comprises a carbon dioxide status indicator, a solvent and a polymer.

The ophthalmic or medical apparatus could be, e.g., a disposable contact lens, a disposable scalpel, a disposable a syringe and/or a disposable ophthalmic lens through which a clinician looks to view a patient's eye.

The color changeable dye can be a first color in the presence of a higher than atmospheric carbon dioxide environment, and can be capable of changing to a second color after exposure to atmospheric conditions for a period of time corresponding to the intended use time of a restricted, disposable or limited use product. In one example, the period of time is less than about 60 minutes. In another example, the period of time is between about 1 and about 168 hours.

Examples of carbon dioxide status indicators include Cresol Red, Texas Red Hydrazine, Bromothymol Blue, M-Cresol Purple, Phenol Red, Congo Red and Natural Red.

Examples of solvents include acetone, alcohol, ethanol, methanol and water.

Examples of polymers include polyvinyl alcohol (PVA), hydroxyethyl cellulose (HEC), hydroxypropyl cellulose (HPC), polyvinyl butyral (PVB), polyvinyl chloride (PVC), polyethylene terephthalate (PET), and polymers made from vinylidene chloride along with other monomers.

The color changeable dye can further comprise a plasticizer and/or an agent to facilitate mixing. In one example, the plasticizer is glycerol. Examples of agents to facilitate mixing are bentonite nanoclay, glass microspheres, diatomaceous earth and cellulose acetate.

According to another embodiment of the present application, an apparatus with time controlled color change indication comprises a restricted, disposable, or limited use apparatus and a color changeable dye disposed on the restricted, disposable or limited use apparatus or its packaging wherein said color changeable dye comprises a carbon dioxide status indicator, a solvent and a polymer.

The apparatus could be, for example, a cosmetic applicator or an oral medication or pill having an expiration date after which said apparatus should not be used.

The color changeable dye can be a first color in the presence of a higher than atmospheric carbon dioxide environment, and can be capable of changing to a second color after exposure to atmospheric conditions for a period of time corresponding to the intended use time of a restricted, disposable or limited use product. In one example, the period of time is less than about 60 minutes. In another example, the period of time is between about 1 and about 168 hours.

Examples of carbon dioxide status indicators include Cresol Red, Texas Red Hydrazine, Bromothymol Blue, M-Cresol Purple, Phenol Red, Congo Red and Natural Red.

Examples of solvents include acetone, alcohol, ethanol, methanol and water.

Examples of polymers include polyvinyl alcohol (PVA), hydroxyethyl cellulose (HEC), hydroxypropyl cellulose (HPC), polyvinyl butyral (PVB), polyvinyl chloride (PVC), polyethylene terephthalate (PET), and polymers made from vinylidene chloride along with other monomers.

The color changeable dye can further comprise a plasticizer and/or an agent to facilitate mixing. In one example, the plasticizer is glycerol. Examples of agents to facilitate mixing are bentonite nanoclay, glass microspheres, diatomaceous earth and cellulose acetate.

These and other advantages and novel features of the present invention, as well as details of illustrated embodiments thereof will be more fully understood from the following description of the drawings.

Figure 1:
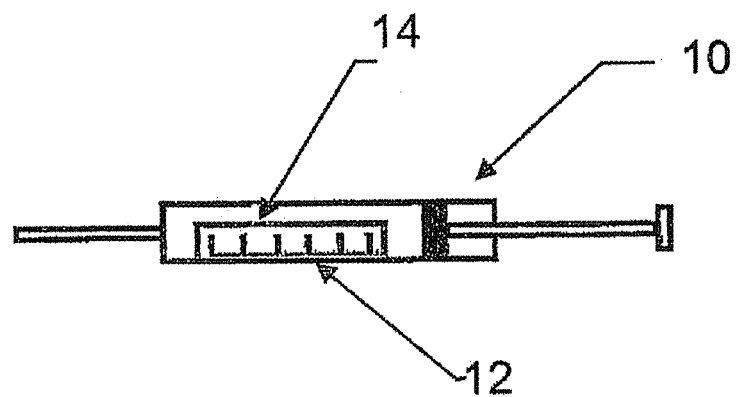
FIG. 1 is a perspective view of a syringe in accordance with one embodiment of the present invention depicting the area of the color changeable dye overlying the graduated scale of the syringe.

The foregoing summary, as well as the following detailed description of certain embodiments of the present application, will be better understood when read in conjunction with the appended drawings. For the purposes of illustration, certain embodiments are shown in the drawings. It should be understood, however, that the claims are not limited to the arrangements and instrumentality shown in the attached drawings. Furthermore, the appearance shown in the drawings is one of many ornamental appearances that can be employed to achieve the stated functions of the system.

DETAILED DESCRIPTION OF THE APPLICATION

A solution of the present application utilizes indicator chemistry to create a color change indication on a product that provides accurate information or a warning to a user of, e.g.: prior use of a single use product or instrument; a reminder that a limited use product has reached its expiration time; or that a product that is restricted for use has been tampered with. The warning indication is provided by a dye that changes color in a time controlled manner wherein the dye is disposed on the product itself by being either printed on the product or incorporated within the material forming a portion of the product, in this manner dyes are understood to include pigments.

A color changeable dye of the present application may include a carbon dioxide status indicator, a solvent, a polymer wherein the carbon dioxide status indicator is dispersed, an optional plasticizer, and an optional agent to facilitate mixing wherein the color changeable dye changes to a warning color after exposure to a change in carbon dioxide environment for a predetermined period. Each of these elements will be explored in more depth below.

A carbon dioxide status indicator is a compound that changes color because it is exposed to a change in carbon dioxide environment, i.e., the additional presence or absence of carbon dioxide either before or after the color change is what triggers the change in color, and is used to indicate a change in the carbon dioxide environment. In one embodiment the carbon dioxide status indicator is a pH status indicator. A pH status indicator is a compound that changes color when exposed to a change in pH and is used to indicate a change in environment. A pH status indicator can be incorporated into the present color changeable dye to allow for a color change upon exposure to a change in carbon dioxide environment. That change could be either an increase or a decrease in the carbon dioxide concentration of the environment. Examples of possible pH status indicators and their corresponding colors are shown below in Table 1.

TABLE 1

| pH Status Indicator | Acid or Low pH Color | pH Transition Range | Base or High pH Color |
|---|---|---|---|
| Cresol Red (CR, o-Cresolsulfonephthalein) | yellow | 7.2-8.8 | reddish-purple |
| Bromothymol blue (BTB, Hydroxy triarylmethane) | yellow | 6.0-7.6 | blue |
| Congo red (sodium salt of benzidinediazo-bis-1-naphthylamine-4-sulfonic acid) | blue-violet | 3.0-5.0 | red |
| Phenol red (PR, phenolsulfonphthalein) | yellow | 6.4-8.0 | red |
| Neutral red (NR, toluoylene red) | red | 6.8-8.0 | yellow |

Texas Red or m-Cresol Purple could also be used. The acid low pH color for these dyes is a light yellow. Texas Red transitions from yellow to red at about 4% $CO_2$. m-Cresol purple transitions from yellow to purple at approx. 2% $CO_2$. It is understood that other status indicators could be substituted in the color changeable dye of the present application. Preferred pH status indicators for use in the present solution are Cresol Red, m-Cresol Purple and Phenol Red.

A pH status indicator is a halochromic chemical compound that is added in small amounts to a solution so that the pH of the solution can be determined visually. A pH status indicator is a chemical detector for hydronium ions ($H_3O^+$) or hydrogen ions ($H^+$) in the Arrhenius model. Normally, the indicator causes the color of the solution to change depending on the pH. The reactions of pH indicators can be simplified as follows:

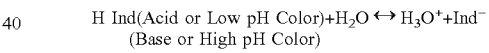

H Ind(Acid or Low pH Color)+$H_2O$ ↔ $H_3O^+$+Ind⁻ (Base or High pH Color)

These reactions and their role in the present color changeable dye will be discussed in more detail below.

As an example of how the pH status indicators function in different carbon dioxide environments, for Cresol Red the acid or low pH color is yellow and the base or high pH color is reddish purple. When the Cresol Red is in a carbon dioxide rich environment, for example a pure 100% carbon dioxide environment, it will be in the H Ind form which is the acid or low pH color of yellow. When placed in a lower carbon dioxide environment, for example an atmospheric environment with approximately 0.0397% carbon dioxide, the Cresol Red changes to its Ind⁻ form which is the base or high pH color of reddish purple. This would apply similarly to the other pH status indicators in the chart above with their respective high and low pH colors.

A benefit of the present application is that the pH status indicator can be incorporated into the color changeable dye in its acid or low pH form (the yellow form in the case of Cresol Red) in a carbon dioxide rich environment. The product can then subsequently be packaged to provide a sterile environment for the product. The internal atmosphere of the package can be pure carbon dioxide (approximately 100% carbon dioxide) or any other amount of carbon dioxide higher than the amount of carbon dioxide in the atmosphere, e.g. 10%, 20%, 30%, 40%, 50%, 60%, 70%, 80%, 90% carbon dioxide.

When the package is subsequently opened and the product is exposed to atmospheric conditions with a lower carbon dioxide content (approximately 0.0397% carbon dioxide), the dye disposed on the product will change from its acid or low PH state (yellow for Cresol Red) to its base or high pH state (reddish purple for Cresol Red) after a period of time that is controlled by the composition of the dye as discussed in detail below, and that is selected to correspond to the typical time for a single use of a product in the case of single use products or that corresponds to the expiration time of the product. The time at which the dye changes color can also be selected so as to indicate that the product may have been tampered with.

The present color changeable dye contains a solvent. The solvent can be added to the color changeable dye to dissolve the carbon dioxide status indicator. Preferred solvents include acetone, alcohol, ethanol, methanol and water.

A benefit of the present color changeable dye is that the color change can be delayed so that it does not begin immediately upon exposure to an atmospheric environment but rather at some predetermined time based on recommended use of the product. For example, the dye could turn color (reddish purple for Cresol Red) after a period of days for a product that is intended to be used for a certain number of days after opening. As another example, the dye could turn color (reddish purple for Cresol Red) after minutes for a product that should be used within minutes of opening. In order to delay the color change of the dye upon exposure a polymer wherein the indicator is dispersed can be included.

A polymer acts to delay the change of the carbon dioxide status indicator by forming a physical or chemical barrier around it. Examples of polymers that the pH indicator can be dispersed in include polyvinyl alcohol (PVA), hydroxyethyl cellulose (HEC), hydroxypropyl cellulose (HPC), polyvinyl butyral (PVB), polyvinyl chloride (PVC), polyethylene terephthalate (PET), or polymers made from vinylidene chloride (especially polyvinylidene chloride or PVDC), along with other monomers, e.g. Saran®.

Other agents can be added to the color changeable dye in order to give the dye physical properties that make it usable for its intended purpose. For example, a plasticizer can be added to the color changeable dye to give it plastic or moldable qualities. A preferred plasticizer is glycerol.

As another example of an agent that gives the dye physical properties that make it usable for its intended purpose, an agent to facilitate mixing lessens the tacky nature of the carbon dioxide status indicator and creates microspheres to help the hygroscopic glycerol mix with an aqueous solvent and form a usable solution. Examples of agents to facilitate mixing include bentonite nanoclay, glass microspheres, diatomaceous earth and cellulose acetate. A preferred agent to facilitate mixing is bentonite nanoclay. The bentonite nanoclay acts to incorporate the viscous, hygroscopic glycerol into the aqueous dye. Without addition of an agent to facilitate mixing, such as bentonite nanoclay, the other components of the solution will not mix as well but separate like a mixture of oil and water. The agent for facilitating mixing, such as bentonite nanoclay, allows these materials to be mixed and form the present color changeable dye.

For single use disposable products the dye may be required to be substantially translucent in its high carbon dioxide environment and change color after exposure to atmospheric conditions after a number of minutes, a number of hours, or a week.

Figure 2:
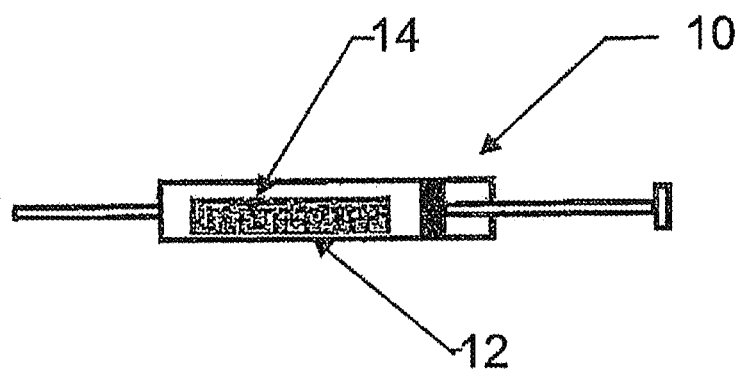
FIG. 2 is a perspective view of the syringe of FIG. 1 depicting the syringe after the timed color change occurs.

For example, the color changeable dye that changes after exposure to atmospheric conditions for a number of minutes could be used with a disposable syringe that is intended for a single use that takes less than 10 minutes. FIG. 1 shows such a disposable syringe 10. The disposable syringe 10 can include a graduated scale 12 printed thereon so that the amount of liquid drawn into the syringe can be accurately measured. In one embodiment, the color changeable dye 14 is printed over the scale. In this embodiment, the dye is substantially translucent so that the scale is clearly visible until the dye 14 changes color, as depicted at 14' in FIG. 2, after a predetermined time associated with the time of typical use of the single use disposable syringe 10. In the embodiment of the syringe depicted in FIGS. 1 and 2, because the dye is disposed over the graduated scale, when the time controlled color change occurs, the graduated scale is no longer clearly visible so that the disposable syringe cannot be accidentally reused. In this manner, the transmission of contaminants or disease from one patient to another by an inadvertent reuse of the syringe is prevented.

Figure 3:
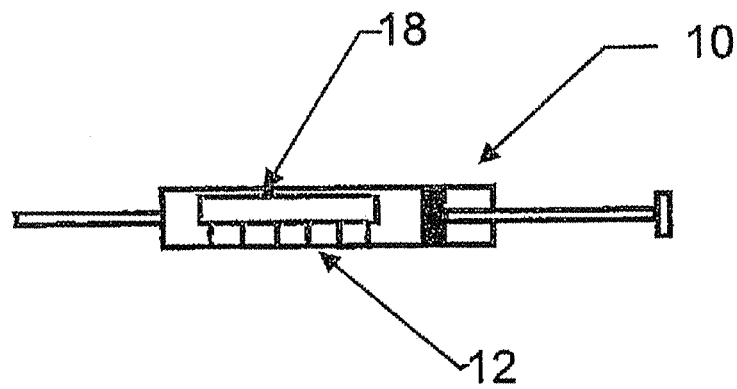
FIG. 3 is an illustration of an alternative placement of the dye on a syringe.
Figure 4:
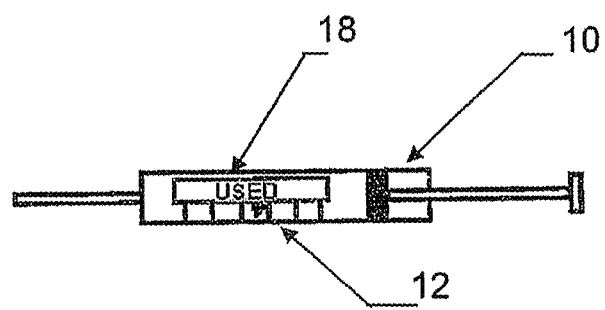
FIG. 4 is an illustration of the syringe of FIG. 3 with an expiration message printed with the color changeable dye which becomes visible after a predetermined period of time.

In another embodiment of the present invention as depicted in FIGS. 3 and 4, the dye is disposed on another area such as 18 of the disposable syringe 10. The dye can be used as an ink to print a message on the disposable product so that when the color change occurs the message, such as the word "USED," becomes visible to the user as shown at 18' in FIG. 4.

Figure 5:
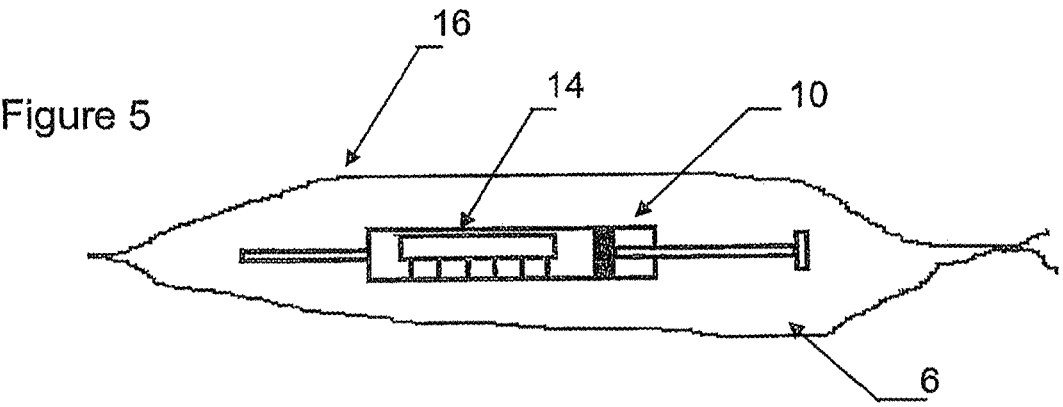
FIG. 5 is a perspective view of the syringe of FIG. 3 contained in a package to prevent premature actuation of the color changeable dye.

The dye of the present invention is applied in its acid or low pH form (yellow for Cresol Red) and dries quickly after being placed on the product. The application of the dye is done in an environment with higher than atmospheric carbon dioxide content. After the dye is dry, the product can be sterilized with any common, low temperature sterilization technique and sealed container or package 16, as depicted in FIG. 5, with an internal atmosphere with higher than atmospheric carbon dioxide content. When the package is subsequently opened and the product is exposed to atmospheric conditions, the dye disposed on the product will change from the acid or low pH form to its colored form (reddish purple for Cresol Red) after five or ten minutes depending upon the makeup of the solution.

Figure 6:
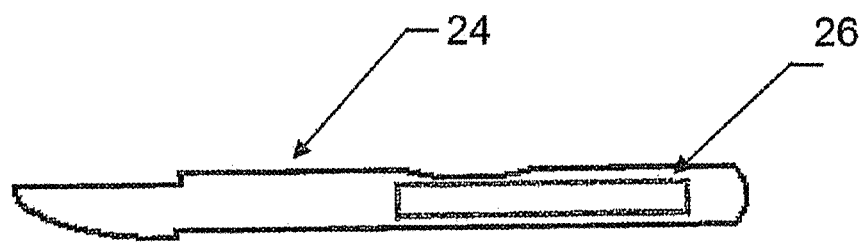
FIG. 6 is a perspective view of a scalpel with the color changeable dye in accordance with another embodiment of the present invention.
Figure 7:
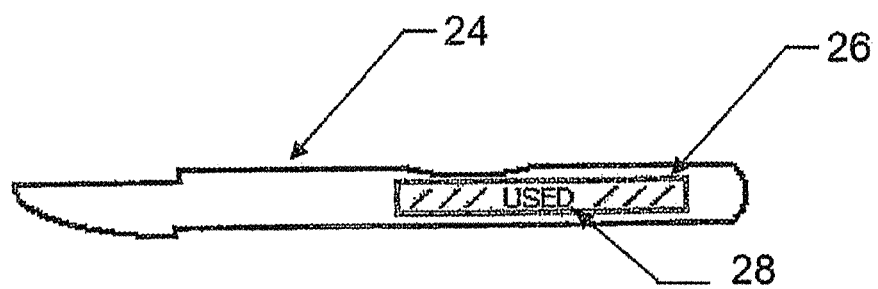
FIG. 7 is a perspective view of the scalpel of FIG. 6 with a message printed with the color changeable dye which has become visible after a predetermined time.

As another example, the color changeable dye that changes after exposure to atmospheric condition for a number of hours could be used with a disposable scalpel that is intended for use in a surgery that takes hours to complete. Such a disposable scalpel is depicted in FIG. 6. The disposable scalpel 24 has the dye 26 of the present invention disposed thereon in an area that will be clearly visible to the surgeon when the dye changes color. As depicted in FIG. 7, a warning message 28 may be printed with the dye on the scalpel to inform the surgeon that the scalpel has been "USED" wherein the color change occurs after a certain number of hours after the scalpel is removed from the higher than atmospheric carbon dioxide content package or container as discussed above with respect to the syringe. In this way, the surgeon is warned that the scalpel should not be inadvertently used again but should be disposed of.

Figure 8:
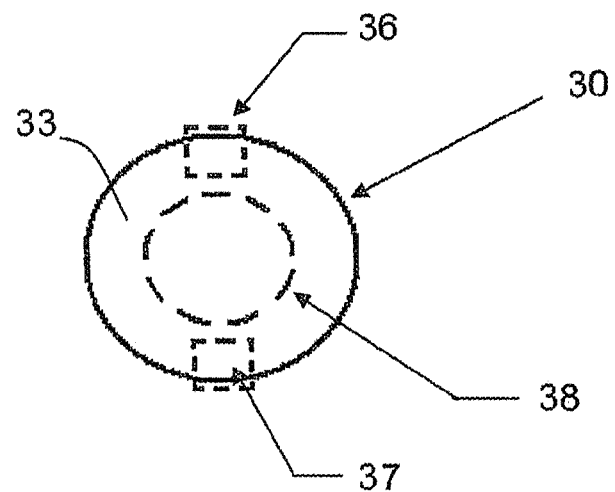
FIG. 8 is a front perspective view of a contact lens in accordance with one embodiment of the present invention with the dye in peripheral areas of the contact lens.
Figure 9:
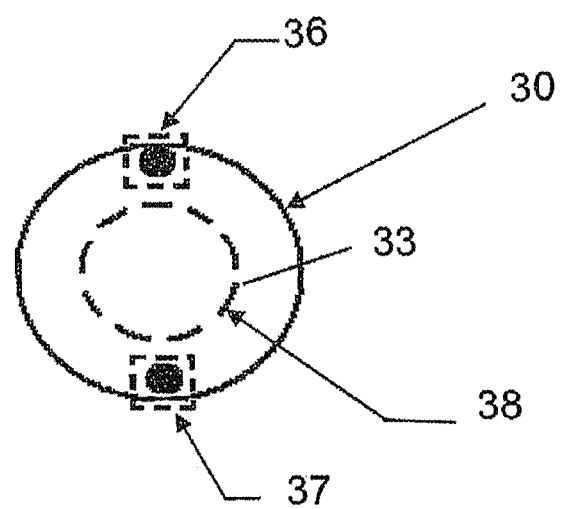
FIG. 9 is a front perspective view of the contact lens of FIG. 8 depicting the dye after color change has occurred to indicate expiration of the lens.
Figure 10:
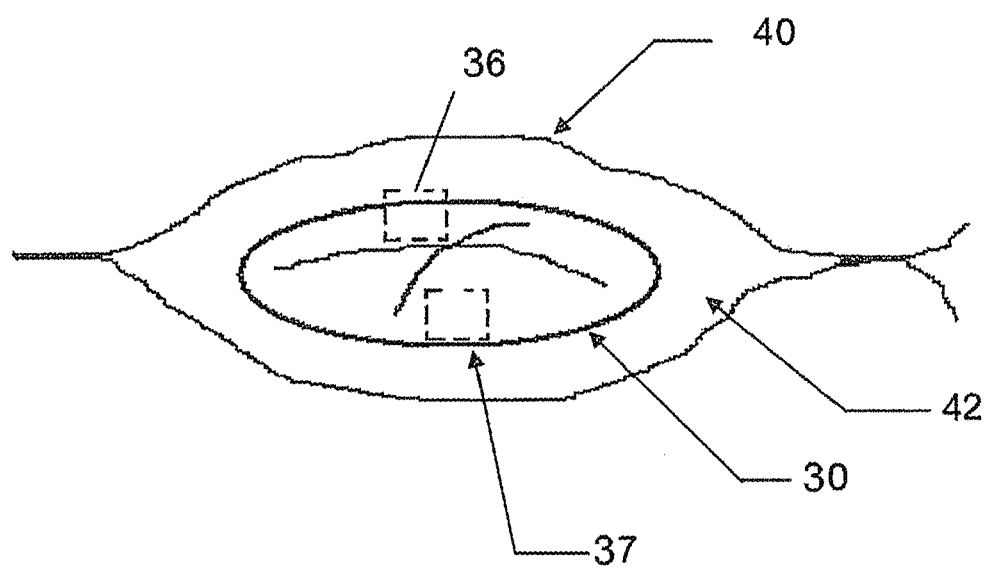
FIG. 10 is a cross-sectional view of a package containing the contact lens of FIG. 8 to prevent premature color change.

As yet another example, the color changeable dye that changes after exposure to atmospheric conditions for a number of days or a week could be used with a disposable contact lens that is only intended for use for a certain number of days or weeks. Such lenses are known as "daily wear" or "monthly wear" disposable contact lenses. The problem that arises with these disposable contact lenses is that many users of the contact lens do not dispose of the contact lens at the recommended time but wear the contact lens longer than they are supposed to. This can damage the eye. The contact lens of the present invention as depicted in FIGS. 8-10 overcomes this problem by providing a visual indication on the contact lens itself that the contact lens should be removed from the eye after the contact lens has been worn for the prescribed amount of time.

In accordance with the present invention, the color changeable dye 36 as described above is disposed on a portion of the contact lens. The formulation for the dye is preferably that which delays the color change of the dye for a certain number of days or weeks according to the longest time that the contact lens manufacturer suggests that the contact lenses should be worn. As discussed above for the other devices, the contact lens 30 should be placed in a higher than atmospheric carbon dioxide content package 40 as shown in FIG. 10. The user of the contact lens 30 can then remove the contact lens from the package for immediate use in the eye. After the contact lens has been worn in the eye for the recommended time by the manufacturer, the color change of the dye occurs as depicted in FIG. 9 wherein, colored (reddish purple for Cresol Red) spots are clearly visible on the contact lens by an observer looking into the contact lens wearer's eye. As such, the contact lens wearer is encouraged to remove the contact lens from his eye and dispose of it as recommended.

As yet another example, the color changeable dye that changes after exposure to atmospheric condition for a number of hours or a week could be used with a product such as makeup or medicine that has a shelf life of certain period of time. For example, it has been found that cosmetic applicators can harbor bacteria that can infect the eye. The dye of the present invention can be applied to the handle of a mascara applicator or eyeliner applicator, for example, so that a warning message becomes visible at the recommended time of replacement, after a number of hours or a week. As such a user is warned that the cosmetic should be disposed of prior to its expiration to prevent eye infections. With regard to medications, the present dye could be applied to oral medications such as pills wherein the dye is printed directly onto the pill and changes color from white or translucent to another darker color or warning symbol when the environmental oxygen level around the pill changes. The color change indication of the dye should be timed to coincide with the expiration of the pills.

In accordance with another embodiment of the present invention, a color change indication on a packaging provides accurate information or a warning to a user: that a product for human consumption within the packaging has reached its expiration time; that a product for human consumption has decreased in freshness, quality of taste or potency or that a product for human consumption within the packaging has been tampered with. The warning indication is provided by a dye that changes color in a time controlled manner wherein the dye is disposed on the packaging by being either printed on the packaging or incorporated within the material forming a portion of the packaging. The dye is safe for human consumption so that it can come into contact with the product for human consumption without any health concerns. In an alternative embodiment, the dye could be printed on the product for human consumption itself without any health concerns.

The dye can be disposed on the interior of the packaging while also being visible from the exterior of the packaging. Disposing the dye on the interior of the packaging allows the color changing dye to monitor the environment inside the packaging where the product for human consumption is contained. Making the dye visible from the exterior of the packaging allows the user to determine the environment on the interior of the packaging where the product for human consumption is contained without opening the packaging.

Figure 11:
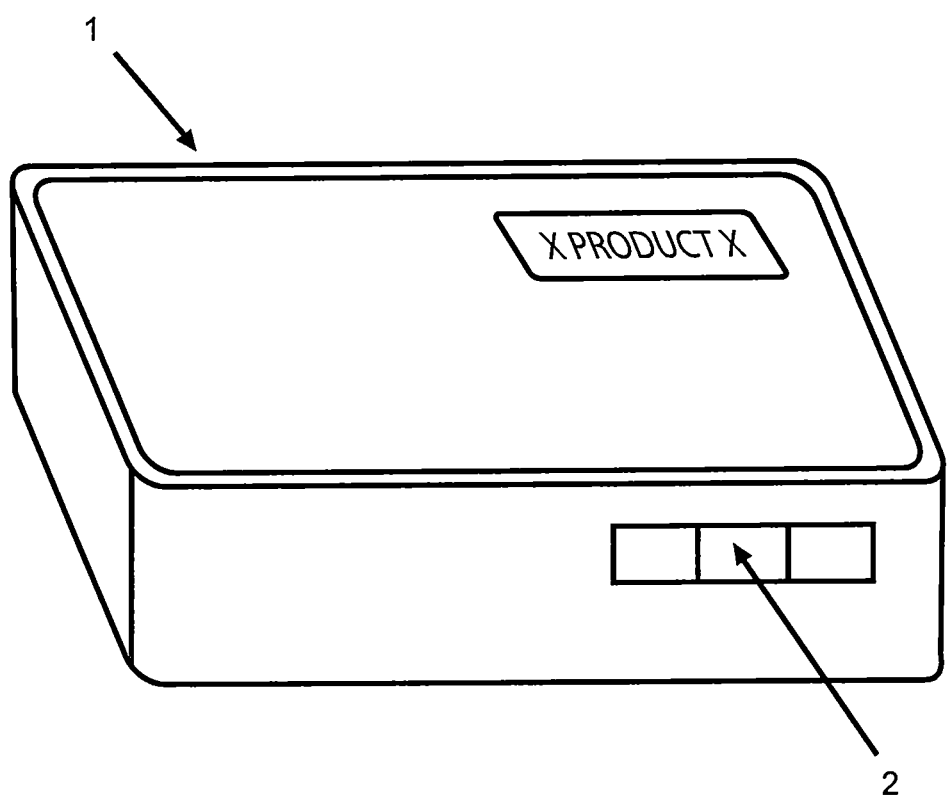
FIG. 11 is a perspective view of a packaging in accordance with one embodiment of the present application depicting the area of the sequential color changeable printed inside the packaging and observable through the closed packaging.

For example, a packaging of the present application could contain a food product on the interior of the packaging. A portion of the food packaging could be a clear material with the color changeable dye located on the interior of the clear portion. The color changeable dye could then be viewed by the user from the exterior while measuring the environment on the interior with the food product. FIG. 11 is a perspective view of a packaging in accordance with one embodiment of the present invention depicting the area of the color changeable dye printed inside the packaging and observable through the closed packaging.

The product for human consumption is packaged into the packaging of the present application to provide a sterile environment for the product and/or limited access thereto. The internal environment of the unopened packaging has a certain percentage of carbon dioxide present. For example the internal environment of the unopened packaging could be "flood packaged" by pumping in carbon dioxide. As an example, a packaging that was flood packaged could have an internal environment of approximately 10%, 20%, 30%, 40%, 50%, 60%, 70%, 80%, or 90% carbon dioxide. In another example, the packaging could by packaged in a vacuum. When the flood packaging or vacuum packaging is subsequently opened, the internal environment and the product for human consumption therein are exposed to a different carbon dioxide environment.

After the product for human consumption is exposed to a change in carbon dioxide environment for a certain period of time, the product for human consumption may reach its expiration or decrease in freshness, quality of taste or potency of the product. The length of the period of time after which a product for human consumption reaches its expiration or decreases in freshness, quality of taste, or potency varies depending on the environment to which the product for human consumption is exposed. For example, a food product will reach its expiration or decreases in freshness or quality of taste more slowly in a closed packaging than in an open packaging. These specific times would differ depending on the internal product. For example, coffee that is exposed to oxygen decreases in freshness and quality of taste very quickly whereas potato chips decrease in freshness and quality of taste more slowly.

After the dye has been exposed to a change in carbon dioxide environment for a certain period of time, the dye which may be disposed on the packaging will change color after a period of time that is controlled by the composition of the dye as discussed in detail herein. The time after which the dye changes color is selected to correspond to the length of the period of time after which a product for human consumption reaches its expiration or decreases in freshness, quality of taste, or potency at a certain percentage of oxygen.

Figure 12:
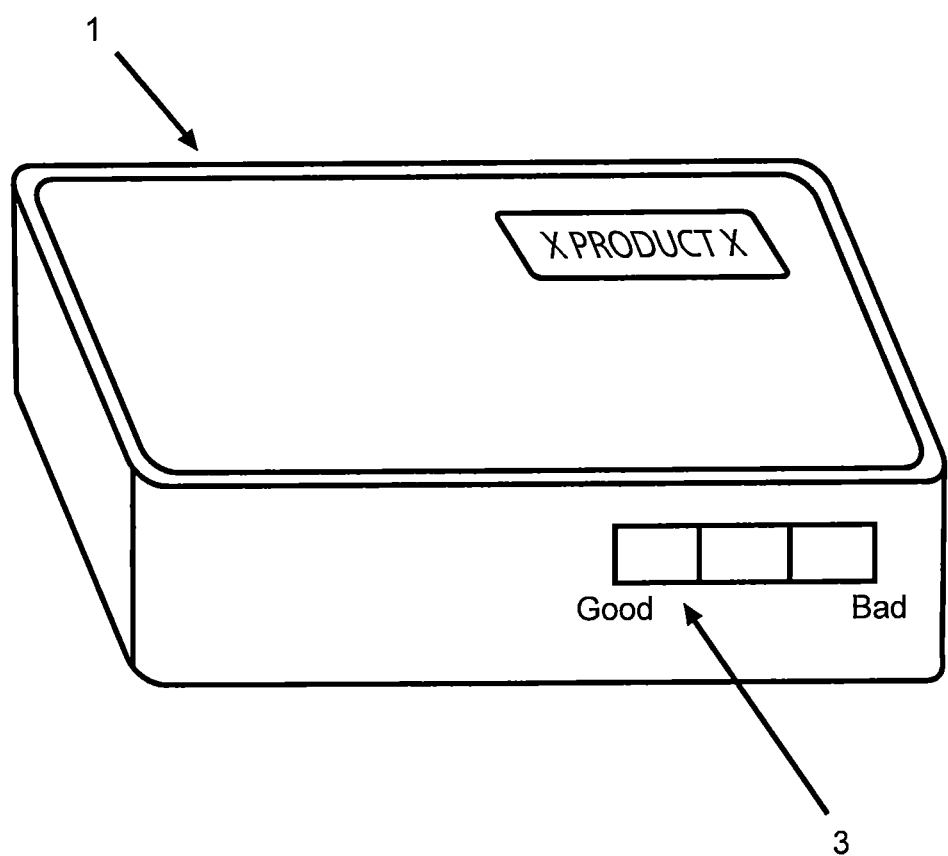
FIG. 12 is an illustration of an oxygen indicator scale showing the freshness information of the inside of a closed packaging.
Figure 13:
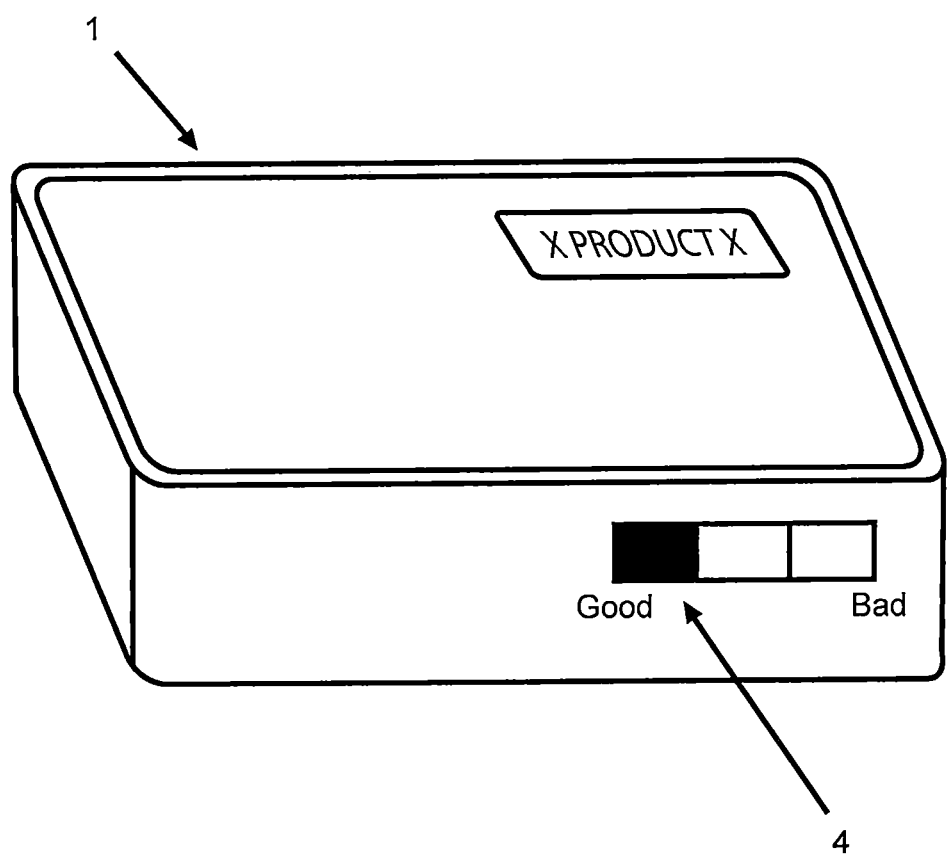
FIG. 13 is an illustration of a packaging of FIG. 1 depicting the packaging and indicator scale after the first in the series of color change occurs.
Figure 14:
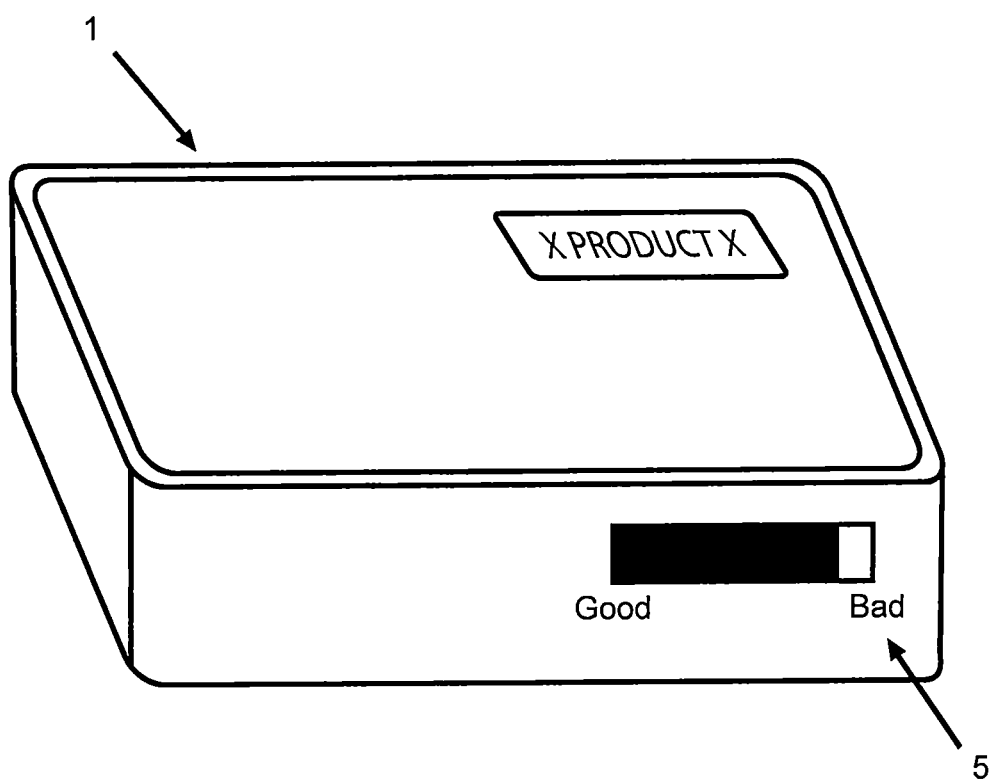
FIG. 14 is an illustration of a packaging of FIG. 1 depicting the packaging after the last in the series of color change occurs.

Different compositions of dye can be disposed on the packaging in a sequential arrangement so the dye changes at different times to indicate a freshness or potency level as the freshness, quality of taste or potency changes. FIG. 12 is an illustration of an indicator scale showing the freshness, quality of taste or potency information of the product inside of the closed packaging. The indicator scale has different compositions of dye at the end of the scale that indicates "good" and the level that indicates "bad." The dyes will change at different times as the product's freshness, quality of taste or potency goes from good to bad. FIG. 13 is an illustration of a disposable packaging apparatus of FIG. 14 depicting the packaging and indicator scale after the first in the series of color change occurs. FIG. 14 is an illustration of a disposable packaging apparatus of FIG. 12 depicting the packaging after the last in the series of color change occurs.

As an example of the sequential indicator, a food product could begin to decline in freshness or quality of taste after two weeks in an open package and continue the decline in an internal environment until its expiration date at one month. The dye at the "good" end of the scale could turn after two weeks, the dye at the middle end of the scale could turn at three weeks and the dye at the "bad" end of scale could turn at one month. This would indicate the level of freshness to the potential purchaser before they purchase and open the product. These specific times are only an example and could be changed to correspond to the internal product. Other words or symbols could be used in this indicator scheme and more levels of indication could be added.

Figure 15:
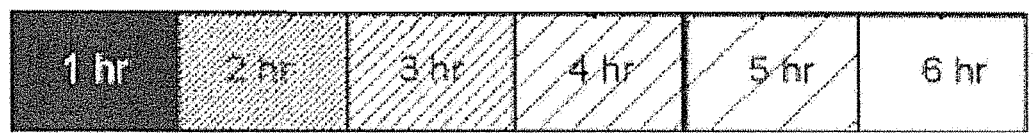
FIG. 15 is an illustration series showing the multi-step printing of the indication in text while the previous text message is blanked out by the newly activated indicator.
Figure 16A:
FIG. 16A-16L are photographs of an exposure time indicator with a color changeable dye that changes color after exposure to an environment in a sequential manner.
Figure 16B:
Figure 16C:
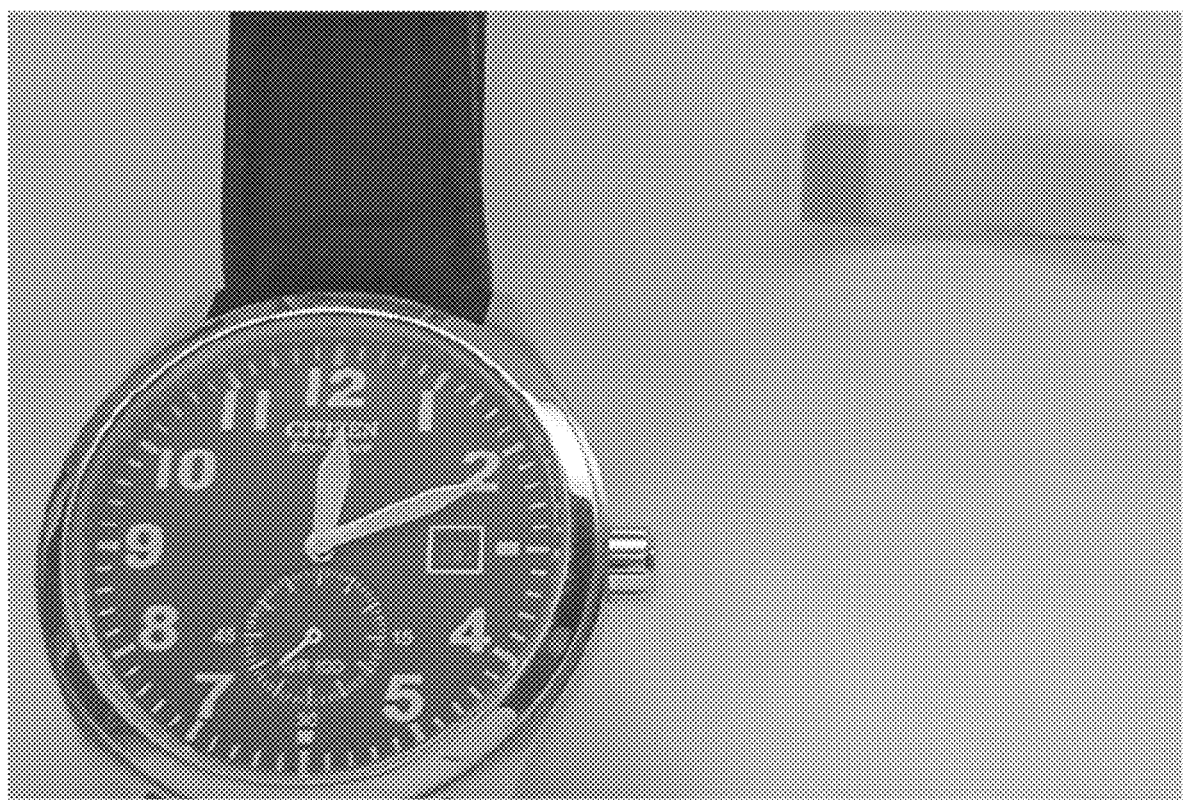
Figure 16D:
Figure 16E:
Figure 16F:
Figure 16G:
Figure 16H:
Figure 16I:
Figure 16J:
Figure 16K:
Figure 16L:

In yet another embodiment of the invention the sequential dye indicators are printed on top of each other, and given that the indicator dye is relatively transparent until activated, the dyes may be printed such that a text message appears indicating the conditions within the packaging and that the previous message is blacked out by the newly activated indicator in the sequence. FIG. 15 is an illustration series showing the multi-step printing of the indication in text while the previous text message is blanked out by the newly activated indicator.

As an example of this sequential indicator, a food product could begin to decline in freshness or quality of taste after two weeks in an open package and continue the decline in until its expiration date at one month. In this example, the term "good" could be written in a first dye that changes almost immediately after the food packaging is opened. A second dye which changes color after two weeks could be applied over the "good" indicator to black it out and the term "ok" could be written in the next area of the scale in that same dye. Finally, a third dye which changes color after four weeks could be applied over the "ok" indicator to black it out and the term "bad" could be written in the next area of the scale in the same dye. In this example, the potential purchaser would see the "good" indicator for the first two weeks when the product is freshest. That indicator would be blacked out after those two weeks and the potential purchaser would see the "ok" indicator during the two weeks after that when the product is starting to decline in freshness but has not yet expired. That indicator would be blacked out after four weeks and the potential purchaser would see the "bad" indicator. These specific times and oxygen levels are only an example and could be changed to correspond to the internal product. Other words or symbols could be used in this indicator scheme and more levels of indication could be added.

It is understood that one can vary particular aspects or volumes of the components of the color changeable dye in order to vary the timing of the color change after exposure to oxygen between a number of minutes, a number of hours or a week. For example, one could vary the type, number or amount of polymer used in the color changeable dye to vary the timing of the color change. Variations in the molecular weight of the polymer could also be used to vary the timing of the color change.

The color changeable dye can be formed as follows. First, a stock solution can be prepared by dissolving a carbon dioxide status indicator in a solvent and 4 mL of 1.0 M sodium hydroxide (ethanol solution). The stock solution can be sonicated until homogeneously mixed.

The carbon dioxide status indicators discussed above could be used in preparing the present stock solution. In one embodiment the carbon dioxide status indicator is Phenol Red. An amount of carbon dioxide status indicator effective to create a color changeable dye that changes to a warning color after exposure to atmospheric condition for a period of time corresponding to the intended use time of a disposable or limited use product is added. For example, 0.5-1.5 grams of carbon dioxide status indicator can be added, or more preferably 1 gram.

The solvents discussed above could be used in preparing the present stock solution. In one embodiment the solvent is ethanol. An amount of ethanol effective to create a color changeable dye that changes to a warning color after exposure to atmospheric condition for a period of time corresponding to the intended use time of a disposable or limited use product is added. For example, 25-35 mL of solvent can be added, or more preferably 30 mL.

10 mL of stock solution is then added to the polymer. If a plasticizer and/or agent to facilitate mixing are used they are also added. The resulting solution can be sonicated until homogeneously mixed.

The polymers discussed above could be used in preparing the present color changeable dye. In one embodiment, the indicator barrier agent is 50% w/v PVB. An amount of polymer effective to create a color changeable dye that changes to a warning color after exposure to atmospheric conditions for period of time corresponding to the intended use time of a disposable or limited use product is added. For example, 10-20 grams of indicator barrier agent can be added, or more preferably 15 gram.

The plasticizers discussed above could be used in preparing the present color changeable dye. In one embodiment, the plasticizer is glycerol. An amount of plasticizer effective to create a color changeable dye that changes to a warning color after exposure to atmospheric conditions for period of time corresponding to the intended use time of a disposable or limited use product is added. For example, 1-2 grams of indicator barrier agent can be added, or more preferably 1.5 gram.

The agents to facilitate mixing discussed above could be used in preparing the present color changeable dye. In one embodiment, the agent to facilitate mixing is bentonite (nanoclay powder). The bentonite can be ground using a mortar and pestle. An amount of agent to facilitate mixing effective to create a color changeable dye that changes to a warning color after exposure to atmospheric conditions for period of time corresponding to the intended use time of a disposable or limited use product is added. For example, 0.8-1.2 gram of an agent to facilitate mixing can be added, preferably 0.9-1.1 gram, or more preferably 1 gram.

Sonication can aid in mixing of the bentonite. The solution can be sonicated for 25-45 minutes or preferably 35 minutes.

The solution can be mixed in a carbon dioxide rich environment. This mixing can last for 25-35 minutes or preferably 30 minutes. The solution can be spread thin and allowed to dry in the carbon dioxide rich environment. The drying can last for hours, preferably 1-2 hours.

The carbon dioxide color changeable dye could then be applied to a substrate. Examples of possible substrates include a sintered material comprised of plastic, metal or other such material, a hydroxyethyl-methacrylate substrate such as that used for hydrophilic contact lenses (daily wear disposables) or a sponge that has been extruded into a filament or a strip and then dipped into the carbon dioxide color changeable dye.

The substrate with the carbon dioxide sensing color changeable dye thereon could then be laminated or encapsulated under a carbon dioxide controlled atmosphere (inclusion of or exclusion of carbon dioxide) between layers of plastic material such as Poly(vinyl chloride), (PVC), Polyethylene terephthalate (PET), or Saran having very low atmospheric diffusion rates; thus forming an indicator strip. Additionally an adhesive back could be applied to the strip to form a sticker type indicator. Under a carbon dioxide controlled atmosphere, the top of the indicator strip would be trimmed or cut off, thus presenting a small atmospheric aperture to the extruded filament or strip.

The indicator strip could then be placed onto, within or around any device or into a package. The package would preferably be flood filled with carbon dioxide. The package would be closed/sealed. Once the package was opened the indicator strip would be exposed to a low carbon dioxide environment. This would trigger the indication of the carbon dioxide sensing color changeable dye through the indicator substrate.

The indication timing control could be adjusted by adjusting the rate of carbon dioxide diffusion out of the indicator substrate, by decreasing the diameter of the aperture thus lengthening the time of the indication, or by making the strip assembly longer. A combination of adjustments such as length and aperture could also be used.

Barriers can also be used to achieve color change at different times. Physical polymer barriers can be applied over the color changeable dye to create color change at different times. A color changeable dye such as those described above can be disposed onto a substrate, such as a paper indicator strip. Polymer sheets, such as polypropelene, are then disposed on top of the color changeable dye. The polymeric sheets in this can be disposed with different numbers of sheets depending on when color change is desired.

FIGS. 16A-L are photographs of a carbon dioxide sensing color changeable dye with stepped polymeric barriers that changes color in a sequential manner after being removed from a carbon dioxide rich environment and exposed to the intended use environment, e.g., an atmospheric environment. The stepped polymer sheets adhered over the paper indicator strip in the example are 0.002 inch thick cellulose. This device has nine regions with no sheets in the first region, one sheet in the second region, two sheets in the third region and so on. The region with no polymeric strips changes color in a matter of minutes. This can be seen in FIGS. 16A-16D. This rapid change indicates that the test strip is working and has been activated. Each 0.002 inch thick cellulose layer provides about a 2 hour barrier for the color changeable dye. The region with one strip changes color after approximately 2 hours, the region with two strips after approximately 4 hours and so on in a controlled sequential manner. This can be seen in FIGS. 16E-16K. The final region has 8 strips and changes after approximately 16 hours. This can be seen in FIG. 16L.

More sheets or thicker sheets will extend the indication time. Conversely, fewer sheets or thinner sheets will decrease the indication time. Additionally using a material that has a higher or lower diffusion of gas will also shorten or lengthen the time respectively. For example, Mylar and Teflon have high low diffusion rates for gases and would lengthen the time before color change of the color changeable dye. Polyethylene has a high diffusion rate for gases and would shorten the time before color change of the color changeable dye. Different gases would also diffusion through the barriers at different rates. For example, carbon dioxide is a smaller molecule and would diffuse through more quickly. The time change can further be timed using this information.

The present color changeable dye can be applied to a disposable, limited or restricted use product. The present color changeable dye can be applied to the product using a number of methods known in the present art. For example, the solution can be applied to the product by printing, painting, spraying, deposition, dipping, flowing or another method known in the art.

While the application has been described with reference to certain embodiments, it will be understood by those skilled in the art that various changes may be made and equivalents may be substituted without departing from the scope of the application. In addition, many modifications may be made to adapt a particular situation or material to the teachings of the application without departing from its scope. Therefore, it is intended that the application not be limited to the particular embodiment disclosed, but that the application will include all embodiments falling within the scope of the appended claims.

The invention claimed is:

1. A method of manufacturing an apparatus with color change indication comprising:
   a packaging comprising a higher than atmospheric carbon dioxide environment;
   a medical device disposed in the packaging;
   a color changeable dye comprising a carbon dioxide status indicator disposed on the medical device; and
   a polymeric barrier disposed on the color changeable dye;
   wherein said color changeable dye is time controlled and configured to change color after exposure to atmospheric conditions for a predetermined time; and
   wherein the carbon dioxide status indicator is incorporated in the dye in a carbon dioxide rich environment.

2. A method of manufacturing an apparatus with color change indication comprising:
   a packaging comprising a higher than atmospheric carbon dioxide environment;
   a medical device disposed in the packaging;
   a color changeable dye comprising a carbon dioxide status indicator disposed on the medical device; and
   a polymeric barrier disposed on the color changeable dye;
   wherein said color changeable dye is time controlled and configured to change color after exposure to atmospheric conditions for a predetermined time; and
   wherein the carbon dioxide status indicator is a pH status indicator and the pH status indicator is incorporated in the dye in an acidic or low pH state in a carbon dioxide rich environment.

3. A method of manufacturing an apparatus with color change indication comprising: providing a medical device; providing a color changeable dye comprising a carbon dioxide status indicator wherein the color changeable dye is configured to change color after exposure to atmospheric conditions for a predetermined time; applying the color changeable dye to a portion of the medical device; applying a polymeric barrier over the color changeable dye where the barrier is configured to alter the predetermined time and where the dye and barrier are configured for the dye to change color at a time indicating that the device is no longer to be used; placing the medical device with the color changeable dye in a packaging; and flood filling the packaging containing the medical device with a higher than atmospheric level of carbon dioxide, wherein the packaging is flood filled with above 80% carbon dioxide.

4. A method of manufacturing an apparatus with color change indication comprising: providing a medical device; providing a color changeable dye comprising a carbon dioxide status indicator wherein the color changeable dye is configured to change color after exposure to atmospheric conditions for a predetermined time; applying the color changeable dye to a portion of the medical device; applying a polymeric barrier over the color changeable dye where the barrier is configured to alter the predetermined time and where the dye and barrier are configured for the dye to change color at a time indicating that the device is no longer to be used; placing the medical device with the color changeable dye in a packaging; and flood filling the packaging containing the medical device with a higher than atmospheric level of carbon dioxide and wherein the packaging is flood filled with above 60% carbon dioxide.

5. An apparatus with color change indication comprising: a packaging comprising a higher than atmospheric carbon dioxide environment; a medical device disposed in the packaging; a color changeable dye comprising a carbon dioxide status indicator disposed on the medical device; and a polymeric barrier disposed on the color changeable dye; wherein said color changeable dye is time controlled and configured to change color after exposure to atmospheric conditions for a predetermined time, and wherein the higher than atmospheric carbon dioxide environment is above 80% carbon dioxide.

6. An apparatus with color change indication comprising: a packaging comprising: a higher than atmospheric carbon dioxide environment; a medical device disposed in the packaging; a color changeable dye comprising a carbon dioxide status indicator disposed on the medical device; and a polymeric barrier disposed on the color changeable dye; wherein said color changeable dye is time controlled and configured to change color after exposure to atmospheric conditions for a predetermined time and wherein the higher than atmospheric carbon dioxide environment is above 60% carbon dioxide.

* * * * *